United States Patent [19]
Jones et al.

[11] Patent Number: 5,750,146
[45] Date of Patent: May 12, 1998

[54] TRANSLUCENT COLLAGEN FORMULATIONS WITH A CYTOTOXIC DRUG

[75] Inventors: Richard E. Jones, Palo Alto; Mike T. Li, Cupertino, both of Calif.

[73] Assignee: Matrix Pharmaceutical, Inc., Menlo Park, Calif.

[21] Appl. No.: 431,084

[22] Filed: Apr. 28, 1995

[51] Int. Cl.$^6$ .............. A61K 9/10; A61K 47/42
[52] U.S. Cl. .......... 424/484; 424/423; 424/426
[58] Field of Search ............ 424/484, 422, 424/423, 426, 409; 252/315.1; 514/544

[56] References Cited

U.S. PATENT DOCUMENTS

| | | | |
|---|---|---|---|
| Re. 33,375 | 10/1990 | Luck et al. | 514/2 |
| 2,589,210 | 3/1952 | McGinty | 167/65 |
| 4,177,263 | 12/1979 | Rosenberg et al. | 424/131 |
| 4,230,687 | 10/1980 | Sair et al. | 424/22 |
| 4,322,398 | 3/1982 | Reiner et al. | 424/19 |
| 4,347,234 | 8/1982 | Wahlig et al. | 424/15 |
| 4,349,530 | 9/1982 | Royer | 424/19 |
| 4,391,797 | 7/1983 | Folkman et al. | 424/19 |
| 4,407,787 | 10/1983 | Stemberger | 424/28 |
| 4,424,208 | 1/1984 | Wallace et al. | 424/177 |
| 4,536,387 | 8/1985 | Sakamoto et al. | 424/14 |
| 4,619,913 | 10/1986 | Luck et al. | 514/2 |
| 4,863,732 | 9/1989 | Nathan et al. | 424/95 |
| 5,002,071 | 3/1991 | Harrell | 424/520 |
| 5,385,738 | 1/1995 | Yamahira et al. | 424/489 |
| 5,490,984 | 2/1996 | Freed | 424/436 |

FOREIGN PATENT DOCUMENTS

| | | |
|---|---|---|
| 0 083 868 | 7/1983 | European Pat. Off. . |
| 0 086 627 | 8/1983 | European Pat. Off. . |
| 55-25806 | 9/1981 | Japan . |

OTHER PUBLICATIONS

Maugh, *Science*, 212:1128–1129 (1981).
Miyata, et al., *Cancer Research*, 43:4670–4675 (1983).
McLaughlin, et al., *Cancer Research*, 38:1311–1316 (1978).
Bier, et al., *Cancer*, 44:1194–1200 (1979).

*Primary Examiner*—Edward J. Webman
*Attorney, Agent, or Firm*—Burns, Doane, Swecker & Mathis, L.L.P.

[57] ABSTRACT

Disclosed are translucent proteinaceous compositions comprising collagen and an effective amount of a compatible cytotoxic drug which compositions are characterized by having a single collagen transition temperature of less than about 45° C. Such compositions possess enhanced retention of the cytotoxic drug at the site of injection and are optically translucent.

18 Claims, 8 Drawing Sheets

TRANSLUCENT COLLAGEN FORMULATIONS WITH A CYTOTOXIC DRUG

BACKGROUND OF THE INVENTION

1. Field of the Invention

This invention is directed to novel collagen/cytotoxic drug compositions. The compositions described herein possess surprising and unexpectedly enhanced drug retention at the site of injection as compared to collagen/cytotoxic drug compositions heretofore disclosed in the art.

2. State of the Art

The treatment of many cellular disorders, for example, tumors, involves the use of cytotoxic drugs. These drugs exert their activity in a variety of ways, usually interfering with a cellular function essential for replication and/or viability of the cell. In many, if not most, instances, the cytotoxic drug is not specific for the unnatural cell, but rather tends to exert its effectiveness due to the more rapid proliferation of the abnormal cell, as compared to normal cells. While many organs of the body of a mammalian host regenerate cells rather slowly, there are also other organs, particularly bone marrow, which involve rapid proliferation of stem cells. Therefore, the cytotoxic agents not only can detrimentally affect the slowly regenerating cells, but also have a particularly pernicious effect on the immune system.

One method to target cytotoxic drug activity toward abnormal cells is set forth by Luck and Brown, U.S. Reissue Pat. No. RE 33,375, which describes treatment of cellular disorders involving abnormal solid cellular growths by introduction of cytotoxic agents dispersed in a physiologically acceptable proteinaceous matrix, such as collagen, into the solid cellular growth or area of an existing or removed solid cellular growth. This patent discloses that the methods described therein provide enhanced effectiveness of the drug on the solid cellular growth with reduced cytotoxic effects on cells distant from the site of introduction. The disclosure of this patent is incorporated herein by reference in its entirety.

While effective against solid cellular growths, the physiological acceptable proteinaceous matrix prepared by Luck and Brown is optically opaque. If such a preparation was clear to translucent, it would be more pharmaceutically elegant.

Notwithstanding the benefits of the methods described by Luck, et al., further reductions in the cytotoxic effects on cells distant from the site of introduction would be particularly beneficial. Additionally, the preparation of a more pharmaceutically elegant composition would also be desirable.

SUMMARY OF THE INVENTION

This invention relates to proteinaceous collagen compositions comprising a cytotoxic drug wherein the composition possesses not only improved drug retention at the site of injection as compared to prior art compositions but is also more pharmaceutically elegant.

The proteinaceous collagen compositions of this invention are characterized by having a single transition temperature of less than about 45° C. In contrast thereto, the proteinaceous compositions of the prior art either have a single transition temperature of greater than 45° C. or have two transition temperatures, one at a temperature of less than about 45° C. and a second at a temperature higher than 45° C. As illustrated in the attached figures, these two transition temperatures evidence themselves as either two separate peaks on Differential Scanning Calorimetry (DSC) curves or as a peak having a shoulder either greater than or less than 45° C.

Surprisingly, it has been found that transformation of prior art proteinaceous collagen compositions to the collagen compositions of this invention enhances the drug retention at the site of injection and provides a pharmaceutically elegant optically translucent composition.

Accordingly, in one of its composition aspects, this invention is directed to a proteinaceous composition in which the protein component comprises from about 30% to about 100% of collagen which protein component is dispersed in an aqueous medium to provide an amorphous flowable mass having a collagen concentration of from about 5 to about 100 mg/mL and an effective amount of a compatible cytotoxic drug wherein the collagen in said proteinaceous composition has a single transition temperature of about 45° C. or less.

In another of its composition aspects, this invention is directed to an optically translucent aqueous collagen composition comprising a proteinaceous material in which the protein component comprises from about 30% to about 100% of collagen wherein said proteinaceous material is dispersed in an aqueous medium at a concentration of from about 5 to about 75 mg/mL to provide an amorphous flowable mass and an effective amount of a compatible cytotoxic drug so that said collagen composition becomes optically translucent when said composition is cooled to about 10° C. or less.

In one of its method aspects, this invention is directed to a method for treating a neoplastic lesion or surrounding tissue which method comprises introducing at the site of the lesion or tissue surrounding the lesion a proteinaceous composition capable of stable placement which composition comprises collagen dispersed in an aqueous medium as an amorphous flowable mass including a sufficient concentration of a compatible cytotoxic drug uniformly dispersed therein so that said collagen has a single transition point of about 45° C. or less whereby said drug is slowly released into the immediate environment thereby avoiding significant levels of the drug at sites distant from the site of introduction.

DETAILED DESCRIPTION OF THE PREFERRED EMBODIMENTS

This invention is directed to novel collagen/cytotoxic drug compositions. In one embodiment, the collagen compositions of this invention are characterized by a single collagen transition temperature of about 45° C. or less. In another embodiment, the collagen compositions of this invention are characterized as optically translucent. However, prior to describing this invention in further detail, the following terms will first be defined:

Definitions

As used herein, the following terms have the following meanings.

The term "transition temperature" means the temperature where the collagen in the aqueous collagen composition undergoes a phase change.

The phase change is typically a change in the fibril size of the collagen in the composition and can be readily determined by a peak in conventional Differential Scanning Calorimetry (DSC) scans of the aqueous collagen composition. For the purposes of this application, transition temperatures measured by DSC are determined under the following conditions: heating at 10°C. per minute at 25 psi nitrogen ($N_2$) using a DSC 10 instrument available from TA Industries, New Castle, Del., USA.

The term "single transition temperature" means that the collagen in an aqueous collagen composition will exhibit a single endothermic peak in a DSC scan over a temperature range of from 30° C. to 70° C. In this regard, DSC scans evidencing a shoulder in the peak are construed herein as having more than a single transition temperature.

The term "compatible cytotoxic drug" means a cytotoxic drug which does not appreciably crosslink to the collagen in an aqueous collagen composition. Appreciable crosslinking of a cytotoxic drug with collagen in an aqueous collagen composition is readily determined as per the examples below by measuring the change in transition temperature of collagen over time at room temperature in the presence of a cytotoxic drug. Specifically, appreciable crosslinking of the cytotoxic drug to the collagen results in a higher transition temperature of the collagen over time and evidences that the drug is not compatible with the collagen.

Suitable compatible cytotoxic drugs include, by way of example only, fluorouracil, methotrexate, etc. and mixtures of compatible cytotoxic drugs. The particular compatible cytotoxic drug or mixture of such drugs employed in the compositions of this invention is not critical. Examples of cytotoxic drugs which appreciably crosslink with the collagen and, accordingly, are not compatible with collagen for the purposes of this invention include, by way of example, cis-diamino dichloroplatinum (II).

The term "an effective amount of a compatible cytotoxic drug" means that a sufficient amount of a compatible cytotoxic drug or mixture of compatible cytotoxic drugs is employed so as to be therapeutically effective for the disease condition being treated while permitting the collagen composition to maintain a single collagen transition temperature of about 45° C. or less.

The term "optically translucent" means that the composition is sufficiently clear in the visible light range as to result in an absorbance of less than 0.6 OD units when measured with light having a wavelength at 410 nm through a 1 millimeter sample of the composition.

Compositions

The compositions described herein are amorphous, optically translucent, injectable, viscous, and have a single transition temperature of about 45° C. or less so as to substantially retain a localized position without significant flow from the site of administration. An important advantage of the compositions of this invention as compared to prior art collagen compositions is that the cytotoxic drug is better retained at the site of injection (i.e., in the tumor) which reduces the degree of transportation of the drug to other sites in the patient. Thus, the circulating blood level of the drug remains low. In this way an enhanced therapeutic gain over direct administration of the cytotoxic drug in the absence of collagen is achieved;

that is, the cytotoxic effect on malignant cells is greater as compared to susceptible normal cells.

Still another important advantage of the compositions of this invention as compared to prior art collagen compositions is that these compositions are optically translucent in the visible light range thereby providing for more pharmaceutically elegant products. That is to say that optically transparent products are generally deemed more pharmaceutically elegant than optically opaque products when employed for injection into a patient.

Without being limited to any theory, it is believed that the optical translucency as well as the enhanced retention of the compatible cytotoxic drug at the site of injection relate to compositions wherein the collagen has a single transition temperature of about 45° C. or less. In turn, it is believed that such compositions are formed through drug diffusion into the collagen fibers which disrupts the fibers thereby forming smaller fibrils. In turn, collagen compositions having smaller fibrils have a higher viscosity and are optically translucent. Again, without being limited to any theory, the higher viscosity of the composition and the significant concomitant reduction in convective transport of the cytotoxic drug into the collagen matrix are believed to correspond to the enhanced retention of the composition and drug dose at the site of injection.

One means for forming the collagen compositions of this invention is through cooling conventional collagen compositions comprising an effective amount of a compatible cytotoxic drug at a temperature of about 10° C. or less (preferably at about 0° to 10° C.) for a sufficient time to permit diffusion of the drug into the collagen fibers. As illustrated in the attached figures, eventual disruption of the collagen fibers into smaller fibrils is evidenced by a change in the transition temperature of the collagen in the collagen composition and conversion of the collagen composition to an optically translucent composition.

The formation of the compositions described herein at reduced temperatures is evidently irreversible (or slowly reversible over months or years) under ambient conditions as evidenced by the fact that cooled compositions remain optically translucent and retain a single collagen transition temperature of about 45° C. or less even when the compositions are returned to room temperature.

Other means contemplated for forming compositions having a single collagen transition temperature of about 45° C. or less include, by way of example, methods which disrupt the fibril size of the collagen in the aqueous composition including, e.g., sonication and other homogenation means, use of high concentrations of certain compatible cytotoxic drugs followed by storage under ambient conditions for prolonged periods of time, etc. However, because of its ease and rapidity of forming such compositions, it is preferred to employ a cooling step to effect formation of a single collagen transition temperature of about 45° C. or less.

The compositions described herein comprise a proteinaceous material in which the protein component comprising from about 30% to about 100% of collagen, a compatible cytotoxic drug and a physiologically acceptable aqueous medium in which the collagen is dispersed and the drug may be dissolved, dispersed or complexed with the collagen. Other materials can optionally be present to enhance the overall beneficial properties of the composition.

The collagen employed in the compositions described herein can be derived from any mammalian host source, such as bovine, porcine or human, or may be prepared, as available, by other techniques, e.g., recombinant DNA techniques. The collagen employed may be natural collagen or may be modified, such as tropocollagen, atelocollagen, or the like. The collagen may be non-immunogenic, immunogenic, or only slightly immunogenic.

Various methods of preparing collagen or derivatives thereof in purified form for administration to a mammalian host are known in the art. Suitable methods include those recited in, for example, U.S. Pat. No. 3,949,073 and references cited therein. Of interest is bovine collagen which is purified and is obtained from young cows or calves. Purification will normally involve dispersion or precipitation from various media, e.g., dilute acetic acid. In some situations, xenogeneic collagen is employed to enhance an immunogenic response in the area of injection or immunogenic adjuvants may be employed. Additionally, collagen suitable for use herein is also commercially available from a number of vendors. Typically, such commercial sources comprise a proteinaceous material wherein the protein component comprises from about 30% to about 100% of collagen with the remainder of the protein component comprising, for example, fibrogen, albumin or derivatives of such proteins.

Sufficient amounts of the proteinaceous material is employed in the aqueous composition to provide for a collagen concentration of from about 5 to about 100 mg/mL and preferably from about 5 to about 75 mg/mL. The specific amount of collagen employed is selected relative to the desired viscosity of the collagen composition such that the composition will flow under moderate pressure, but not move significantly after being positioned at a particular site in the patient. Preferably, sufficient collagen is employed such that the composition will have a viscosity of from about 5,000 to about 20,000 centipoise at 20° C. and at a shear rate of 15.8 $sec^{-1}$.

An effective amount of a compatible cytotoxic drug is also employed in the aqueous collagen compositions described herein. In general, the effective amount of cytotoxic drug will vary from drug to drug and this amount can be readily determined by methods described herein.

Specifically, compositions employing differing amounts of the compatible cytotoxic drug in the aqueous collagen composition, but otherwise similar, are cooled and stored for a period of not less than 24 hours to determine the minimum amount of compatible cytotoxic drug necessary to provide compositions having a single collagen transition temperature of about 45° C. or less.

The compatible cytotoxic drug can be used individually or in combination, depending upon the nature of the drug, the tumor, and whether cooperative action is pharmaceutically indicated. Preferably the compatible cytotoxic drug is fluorouracil, methotrexate or combinations thereof. In a particularly preferred embodiment, the fluorouracil is employed at a concentration of greater than about 20 mg/mL and still more preferably from greater than about 20 mg/mL to about 60 mg/mL in the composition whereas the methotrexate is employed at a concentration of at least 10 mg/mL and still more preferably from about 10 mg/mL to about 60 mg/mL in the composition.

The compatible cytotoxic drug may be bound or unbound to the collagen through non-covalent binding such as complexation, salt formation, coordination complexes, or the like, but any binding should not result in significant diminution of the physiological activity of the drug nor should it result in crosslinking of the collagen fibers. The compatible cytotoxic drug can be modified by, for example, introduction of bonds which allow for enzymatic cleavage, e.g., hydrolysis, of the drug from a carrier other than collagen.

Optionally, various techniques can be employed to diminish drug migration upon injection into a neoplastic lesion or surrounding tissue. For example, the compatible cytotoxic drug can be coupled to specific ligands, such as lipids, phospholipids, peptides, amino acids, sugars, or the like.

These modifications will depend upon the individual drug, varying the solubility of the drug in the aqueous medium and providing for non-covalent interactions with the collagen. In addition, various physiologically acceptable bulking agents or concentrating agents may be optionally employed which serve to provide for drug and protein interactions, with resulting reduction in the rate of drug release. Illustrative materials include inorganic substances, such as hydroxyapatite and organic substances such as carbohydrates, e.g., dextran, agarose, methyl cellulose and cellulose.

The compositions of this invention may still further include other drugs in combination with the compatible cytotoxic drugs so as to reduce physiological insult and enhance therapeutic gain. Of particular interest are agents which restrict regional vasculature, either as to growth and/or passage opening, e.g., vasoconstrictive or sympathomimetic agents. These agents may include catechol amines, e.g., epinephrine and norepinephrine, dipivefrin, epinephryl borate, ergot alkaloids, prostaglandins, angiotensin or the like. Other agents for affecting tissue architecture include enzymes which can injure the stroma, such as the peptidases papain, chymopapain, trypsin, amylase, collagenase and chymotrypsin. Or agents affecting cellular permeability may be employed, such as non-ionic detergents, e.g., polysorbate, amphotericin B, dimethylsulfoxide, and anaesthetics such as procaine. In a particularly preferred embodiment, epinephrine is employed in conjunction with the collagen composition and is added to the composition just prior to use.

Besides using xenogeneic collagen, other materials may be included to enhance an immunogenic response, e.g., proliferation and invasion of macrophage, helper T-cells, etc. Illustrative adjuvants include *Corynebacterium parvum*, Bacillus Calmette-Guerin cell wall or cell wall skeleton preparations. *Mycobacterium bovis* strain, and the like. See, for example, Miyata et al., *Cancer Res.*, 43:4670–4675 (1983); Bier et al., *Arch. Otorhinolaryngol*, 236:245–255 (1982); and Mehanjhlin et al., *Cancer Res.*, 38:1311–1316 (1978) which references are incorporated herein by reference in their entirety.

For enhancing cytotoxic activity various adjuvant materials may be incorporated into the collagen, such as radioactive pellets, e.g., radionuclides technetium or iridium; radiation sensitizers, e.g., misonidazole; repair inhibitors, e.g., methylated xanthines; bioreductive agents, which are activated only in hypoxic cells; immunomodifiers, such as interferons, lymphokines, such as interleukin-2, tumor growth inhibitors, such as tumor necrosis factor, tumor growth factor-β, and the like, and/or angiographic contrast media.

The collagen, cytotoxic drug and certain optional additives are uniformly dispersed in a physiologically acceptable aqueous medium, such as saline, phosphate buffered saline, distilled water, etc. to form a collagen composition. The aqueous medium will be sufficient to provide for an amorphous dispersion capable of flowing under mild pressure. Usually, the liquid aqueous medium will be at least 90 weight percent of the entire composition, more usually at least 95% weight percent, usually not more than about 99.5 weight percent, so as to provide a flowable mixture. The amount will vary depending upon the nature of the compatible cytotoxic drug(s), the presence of other materials and the like.

Optional additives can also be included in the composition for a variety of purposes. These additives will for the most part impart properties which protect the stability of the composition, control the pH, or the like. Illustrative agents include phosphate and acetate buffers, methyl or propyl paraben, polyethylene glycols, and the like. These agents will generally be present in less than about 2 weight percent of the total composition, usually less than about 1 weight percent, and individually may vary from 0 to about 1 weight percent.

The compositions described herein can be prepared by combining the proteinaceous material comprising collagen, the compatible cytotoxic drug and the physiologically acceptable aqueous medium in a sterile environment. Optional additives may also be included at this time although certain additives such as vasoconstrictive or sympathomimetic agents, due to stability problems, may preferably be incorporated into the composition just prior to use. The collagen will be provided in a convenient form, usually admixed with at least a portion of the total aqueous medium to be employed. The composition will be sufficiently workable that upon admixture, a uniform dispersion can be obtained. The compatible cytotoxic drug may be added to the collagenous dispersion with agitation to ensure the uniform dispersion of the drug. Optional materials, as appropriate, may be added concomitantly or sequentially. Sterilization will usually be achieved using aseptic conditions.

After ensuring the uniform dispersion of the various components in the mixture, the mixture is filled and sealed in appropriate containers. At this point, the composition is optically opaque in the visible light range and exhibits two transition temperature on a DSC scan running from 30° C. to 70° C. The first transition temperature is at approximately 45° C. and the second at approximately 55° C.

In one embodiment, the composition is then cooled to a temperature of about 10° C. or less. Cooling is maintained for a sufficient period of time such that the collagen fibers are disrupted, apparently by the compatible cytotoxic drug, into smaller fibrils as evidenced by a change in the transition temperature profile of the collagen in the composition to a single transition temperature at about 45° C. or less. Additionally, upon cooling, the collagen composition is converted to an optically translucent composition. Upon conversion of the composition to one having a single collagen transition temperature of about 45° C. or less, the composition can optionally be warmed to room temperature while retaining the desired single transition temperature.

Other embodiments contemplated as above for converting the collagen composition to an optically translucent composition can be also be employed, when appropriate, at this time.

Utility

The subject compositions are useful in the chemotherapeutic (cylotoxic) treatment of a wide variety of neoplastic lesions involving solid abnormal tumors, cellular growth, or adjacent tissues which may contain abnormal tumor cells. The composition is injected into the lesion, e.g., tumor or lesion area (tissue adjacent to the lesion), or in those situations where the tumor has been removed, tissue adjacent to the previously removed tumor. The composition is flowable for injection, but provides for stable placement, once injected into the tissue. That is, once injected the collagen resists mechanical disruption and does not migrate significantly. After injection, the cytotoxic drug is released into the immediate environment, so as to prevent substantial transportation of the drug to other sites, where its cytotoxic activity is undesirable.

Illustrative tumors include carcinomas, sarcomas and melanomas, such as basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, colorectals cancer, brain tumors, mycosis fungoides, Hodgkin's lymphoma, polycythemia Vera, chronic granulocytic leukemia, lymphomas, oat cell sarcoma, and the like. Tumors may also include benign growths such as condylomata acuminata (genital warts).

The subject composition will be administered to a tumor to provide a cytotoxic amount of a compatible cytotoxic drug at the tumor site. The amount of cytotoxic drug administered to the tumor site will preferably range from about 0.01 to 100, more usually about 0.5 to 30 mg/kg of host, depending upon the nature of the drug, size of the tumor, and other considerations. When employed, the vasoconstrictive agents will generally be present in from about 1 to about 50 weight percent of the compatible cytotoxic drug. With each drug in each tumor, the specific amount of cytotoxic drug employed will depend on factors such as the type and/or nature of the tumor to be treated, the compatible cytotoxic drug to be used, the relative mobility of the cytotoxic drug, and the like. Such factors are well within the skill of the art.

One or more administrations of the subject compositions may be employed, depending upon factors such as the lifetime of the compatible cytotoxic drug at the tumor site and the response of the tumor to that drug. Administration may be by syringe, catheter or other convenient means allowing for introduction of a flowable composition into the tumor. Administration may be every three days, weekly, or less frequent, such as biweekly or at monthly intervals.

Illustrative of the manner of administration according to this invention would be administration of a composition comprising fluorouracil having a single transition temperature of about 45° C. or less. In a preferred embodiment, concentrations of the fluorouracil in the collagen vary from greater than about 20 to about 60 mg/mL. Injection may be at one or more sites depending upon the size of the lesion. Needles of from about 18 to 30 gauge in diameter are convenient. For multiple injections, templates with pre-drilled holes may be employed. The dose of compatible cytotoxic drug will normally be less than 100 mg/m$^2$ of patient and preferably from about 0.01 to about 100 mg/m$^2$ of patient.

The subject methods find particular advantage with tumors or lesions which are clinically relevant. The compositions provide therapeutic gain with tumors greater than 100 mm$^3$, more particularly, greater than 150 mm$^3$, in volume.

The subject method is also found to reduce local inflammation as a result of drug administration. Therefore, local or adjacent tissues are less likely to be affected by the drug. Furthermore, due to the low migratory level of the drug from the site of placement, higher drug dosages can be administered to the site without adverse affects to normal tissue distant from the placement site or to lymphocytes.

The subject method finds advantage in conjunction with other forms of therapy. The lesions may be irradiated prior and/or subsequent to administration of the aqueous collagen composition containing the compatible cytotoxic drug. Dose rates may vary from about 20 to 250 rad/min, usually 50 to 150 rad/min, depending on the lesion, period of exposure, the condition of the patient, and the like. Hyperthermia (heat) may be used as an adjunctive treatment. Treatment will usually involve heating up to about and including 43° C. for about 5 to 100 minutes.

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

cisplatin=cis-diamino dichlororplatinum (II)

cps=centipoise

DSC=Differential Scanning Calorimetry fluorouracil=5-fluorouracil [5-fluoro-2,4-(1H, 3H)pyrimidinedione] [or 5FU]

g=gram

M=molar mg=milligrams mL=milliliters mm=millimeter

OD=optical density

RT=room temperature

EXAMPLES

In the following examples, Examples 1 through 3 illustrate the effect on the collagen transition temperature of aqueous collagen compositions containing various cytotoxic drugs which compositions are maintained at either room temperature (RT) or refrigerated at less than 10° C.

Example 4 illustrates the effects on optical opacity as measured by the absorbance of an aqueous collagen composition comprising collagen and fluorouracil (33.3 mg/mL) due to storage at three different temperatures whereas Example 5 measures the effects of different concentrations of fluorouracil on this absorbance.

Example 6 demonstrates an alternative means for obtaining optical clarity for aqueous collagen composition containing methotrexate.

Examples 7 and 8 illustrate the effects on optical opacity as measured by the absorbance of an aqueous collagen composition comprising collagen and different buffers at different pHs (Example 7) or different additives (Example 8).

Example 9 illustrates that the compositions of this invention have enhanced drug retention at the site of injection into the patient.

Example 1—Effect on the Collagen Transition Temperature of an Aqueous Collagen Composition Comprising Fluorouracil An aqueous collagen composition was prepared by combining requisite amounts of components under aseptic conditions to provide for an aqueous collagen composition comprising 6.5 weight percent collagen, 0.1M sodium phosphates and 0.045M sodium chloride. A DSC scan of the resulting composition was conducted by adding an aliquot of the composition to the sample holder (DSC pan), hermetically sealing the sample holder, and then placing the holder into a Differential Scanning Calorimeter (Model No. DSC 10 available from TA Instruments, New Castle, Del., USA). The calorimeter measures the transition temperature correlating to a phase change in the collagen composition by recording the temperature where excess heat over baseline is either absorbed or released by the composition.

Figure 1:
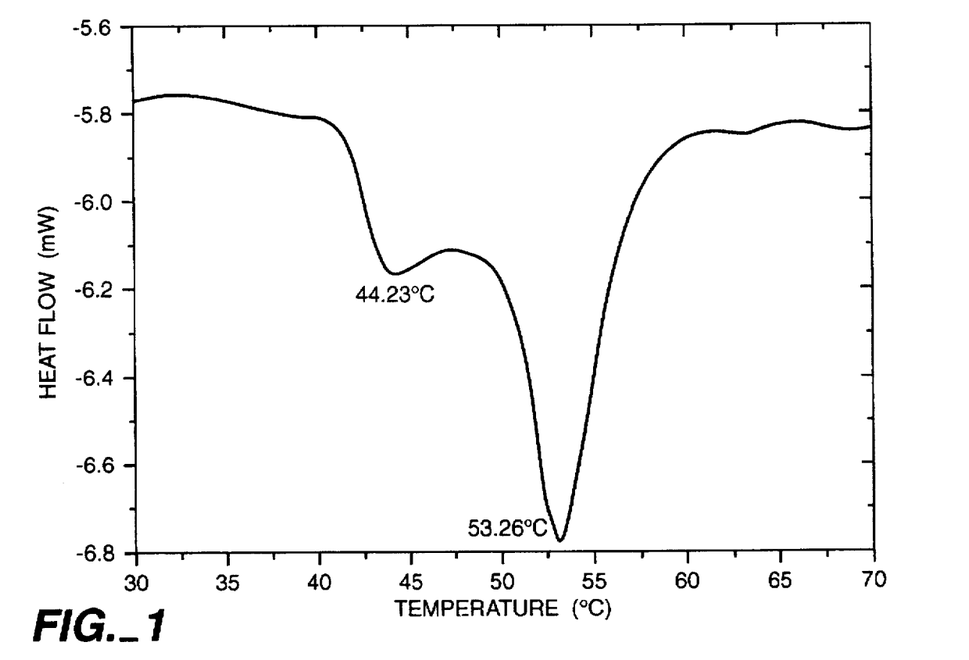
FIG. 1 illustrates a Differential Scanning Calorimetry (DSC) scan from 30° C. to 70° C. of an aqueous composition comprising 6.5 weight percent collagen. This scan illustrates two collagen transition temperatures, the first at about 44° C. and the second at about 53° C.

The DSC scan of this composition was then conducted at from 30° to 70° C. at the rate of 10° C. per minute and the results are illustrated in FIG. 1. This figure shows that the aqueous collagen composition exhibits two transition temperatures, one at about 44.2° C. and the other at about 53.3° C.

Two additional aqueous compositions were prepared as above with the exception that fluorouracil was incorporated into each of these compositions and the resulting composition comprised collagen (2.2 weight percent), fluorouracil (33.3 mg/mL), 0.033M sodium phosphates and 0.015 M sodium chloride. The compositions were formulated by mixing under aseptic conditions, until homogeneous, 1 volume of an aqueous collagen composition comprising 6.5 weight percent collagen, 0.1M sodium phosphate and 0.045M sodium chloride with 2 volumes of a fluorouracil solution (50 mg/mL) at ambient conditions by recirculation through a static mixer and with magnetic stirring. After formulation, both compositions were optically opaque.

The first composition was then stored at room temperature whereas the second composition was stored under refrigeration at a temperature of from about 2° C. to about 8° C. After storage for not less than 24 hours, the first composition was still optically opaque whereas the second composition had become optically translucent. A DSC scan of each of these samples was then conducted in the manner described above. The results of these scans are illustrated in FIGS. 2 and 3 respectively.

Figure 2:
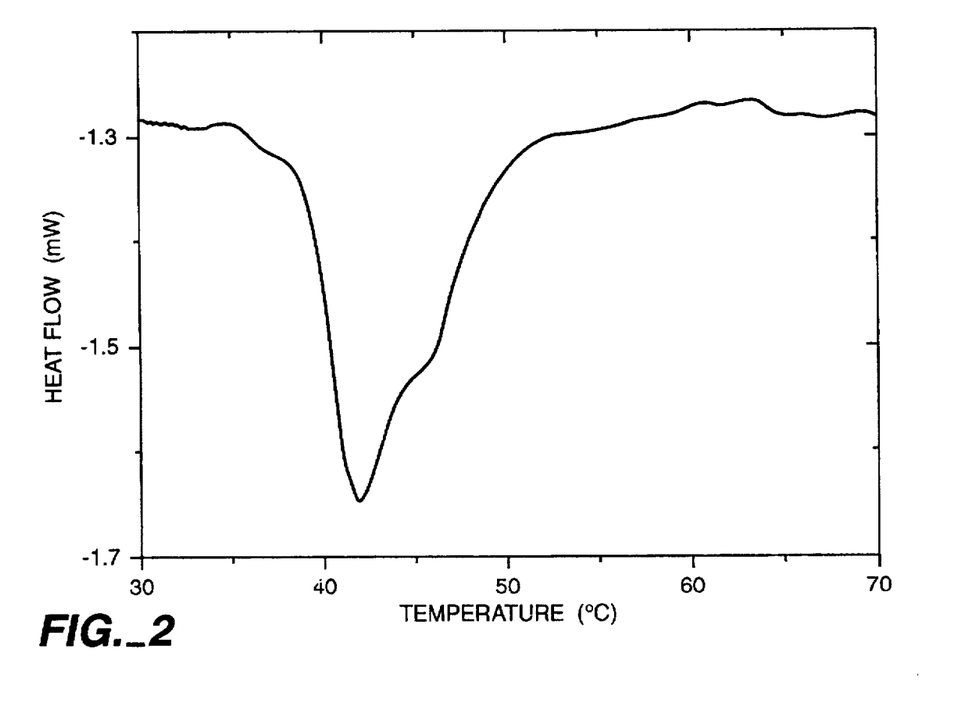
FIG. 2 illustrates a DSC scan from 30° C. to 70° C. of an aqueous composition comprising 2.2 weight percent collagen and 3.3 weight percent fluorouracil stored at room temperature. This scan illustrates that this composition exhibits two collagen transition temperatures, the first at about 42° C. and the second appearing as a shoulder at about 45° to 46° C.
Figure 3:
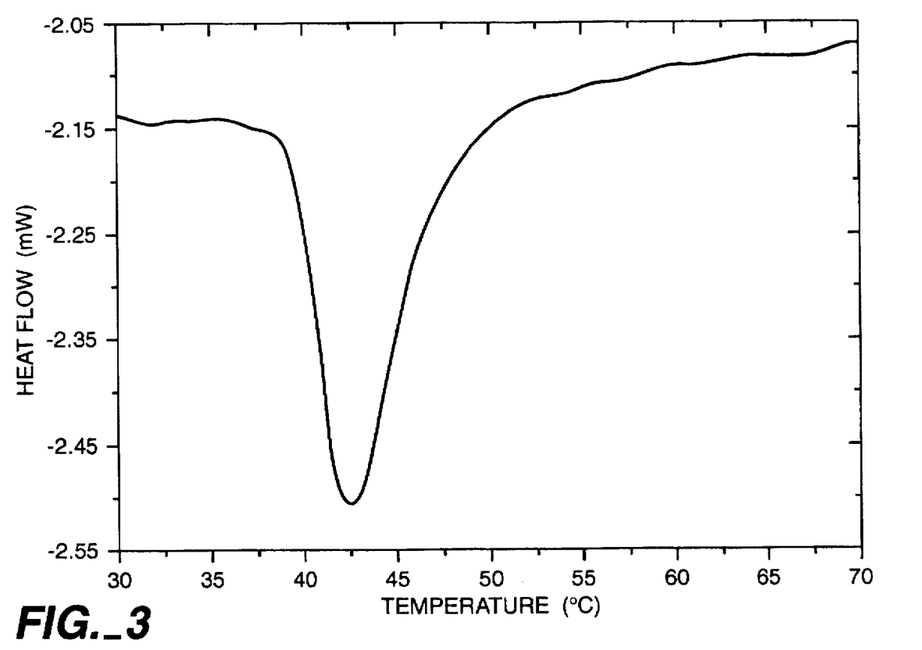
FIG. 3 illustrates a DSC scan from 30° C. to 70° C. of an aqueous composition comprising 2.2 weight percent collagen and 3.3 weight percent fluorouracil. After formulation, the composition was stored in a refrigerator at about 4° C. for no less than 24 hours. Upon removal from the refrigerator, the composition was optically translucent and the DSC scan illustrates that this composition exhibits a single collagen transition temperature at about 42.5°C.

Specifically, FIG. 2 illustrates that the aqueous collagen composition comprising fluorouracil and stored at room temperature has two collagen transition temperatures, the first at about 42° C. and the second appearing as a shoulder at about 45° to 46° C. Contrarily, FIG. 3 illustrates that the same aqueous collagen composition stored under refrigeration for the same period of time has a single collagen transition temperature of about 42.5° C.

In addition to the above, the viscosity at 20° C. of the aqueous collagen compositions comprising fluorouracil stored at room temperature and at 2° to 8° C. was compared as well as the optical absorbance of these compositions measured through a microcuvet with a 1 mm pathlength using light at a wavelength of 410 nm. The results of this analysis are set forth in Table I below:

TABLE I

| Collagen composition stored at | Viscosity (centipoise at 20° C.) | Optical Absorbance (at 410 nm) |
| --- | --- | --- |
| RT | 6478 cps | 0.684 OD |
| 2° to 8° C. | 7873 cps | 0.009 OD |

In view of the results of this example, fluorouracil is a compatible cytotoxic drug.

Example 2—Effect on the Collagen Transition Temperature of an Aqueous Collagen Composition Comprising Methotrexate An aqueous collagen composition was prepared by combining requisite amounts of components under aseptic conditions to provide for an aqueous collagen composition comprising 6.5 weight percent collagen, 0.1M sodium phosphates and 0.045M sodium chloride. A DSC scan of the resulting composition was conducted by adding an aliquot of the composition to the sample holder (DSC pan), hermetically sealing the sample holder, and then placing the holder into a Differential Scanning Calorimeter (Model No. DSC 10 available from TA Instruments, New Castle, Del., USA). The calorimeter measures the transition temperature correlating to a phase change in the collagen composition by recording the temperature where excess heat over baseline is either absorbed or released by the composition.

Figure 4:
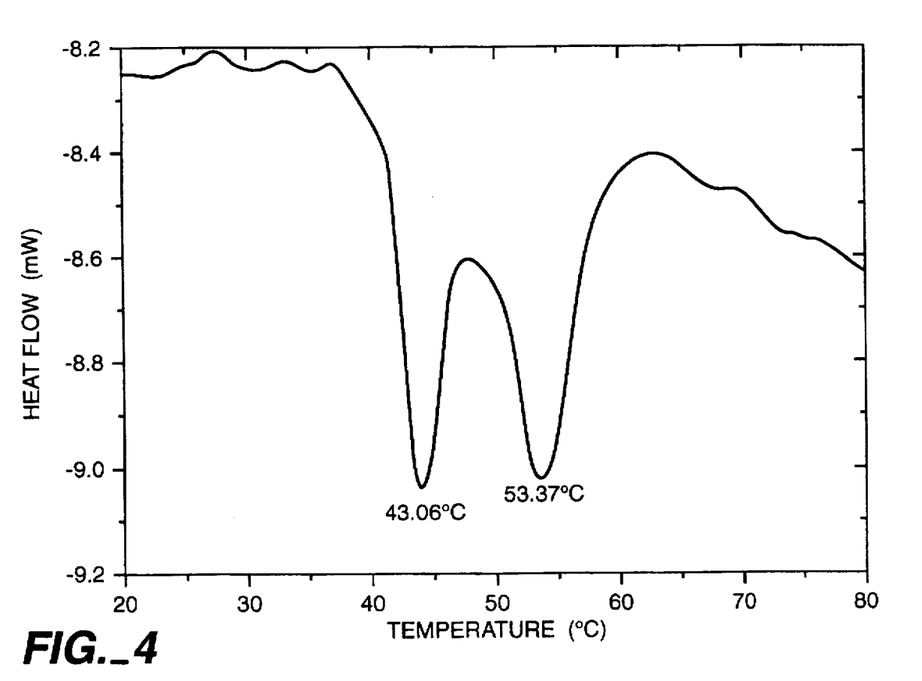
FIG. 4 illustrates a DSC scan from 20° C. to 80° C. of an aqueous composition comprising 6.5 weight percent collagen prepared at room temperature. This scan illustrates that this composition two collagen transition temperatures, the first at about 43° C. and the second at about 53° C.

The DSC scan of this composition was then conducted at from 30° to 80° C. at the rate of 10° C. per minute and the results are illustrated in FIG. 4. This figure shows that the aqueous collagen composition exhibits two transition temperatures, one at 43° C. and the other at about 53° C.

Two additional aqueous compositions were prepared as above with the exception that methotrexate was incorporated into each of these compositions and the resulting composition contained collagen (2.2 weight percent), methotrexate (16.7 mg/mL), 0.033M sodium phosphates and 0.015M sodium chloride. The compositions were formulated by mixing under aseptic conditions, until homogeneous, 1 volume of an aqueous collagen composition comprising 6.5 weight percent collagen, 0.1M sodium phosphates and 0.045M sodium chloride with 2 volumes of a methotrexate solution at ambient conditions. Mixing was conducted by repeated transfers between two syringes connected by a mixing adapter. The first composition was stored at room temperature whereas the second composition was stored under refrigeration at a temperature of from about 2° C. to about 8° C. After storage for approximately 1 month, the first composition was still optically opaque whereas the second composition had become optically translucent. A DSC scan of each of these samples was then conducted in the manner described above. The results of these scans are illustrated in FIG. 5 and 6, respectively.

Figure 5:
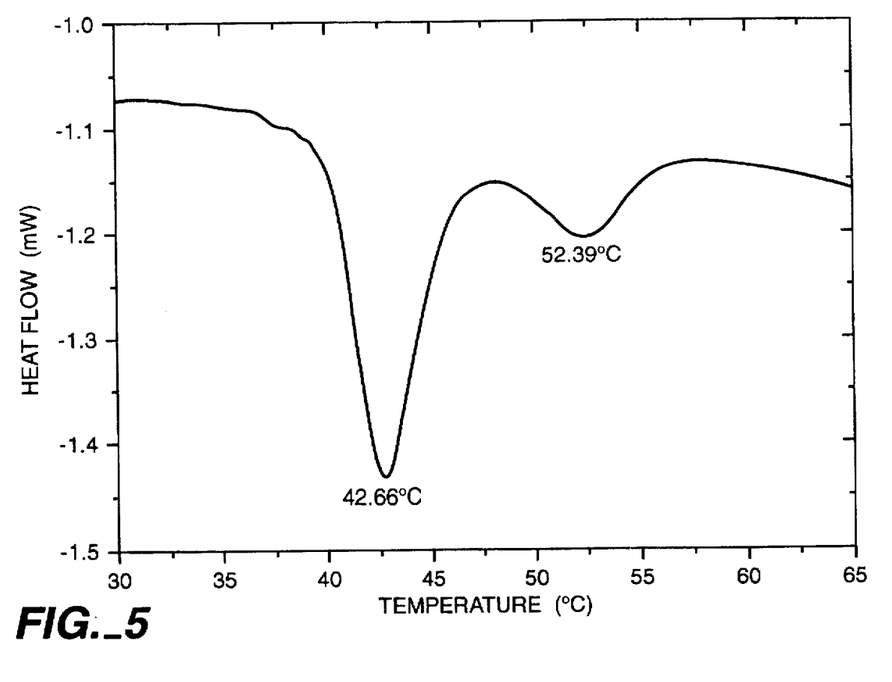
FIG. 5 illustrates a DSC scan from 30° C. to 65° C. of an aqueous composition comprising 2.2 weight percent collagen and 16.7 mg/mL methotrexate. After formulation, the composition was stored at room temperature for 1 month and was optically opaque after storage. A DSC scan illustrates that this composition exhibits a first collagen transition temperature at about 43° C. and a second transition point at about 52° C.
Figure 6:
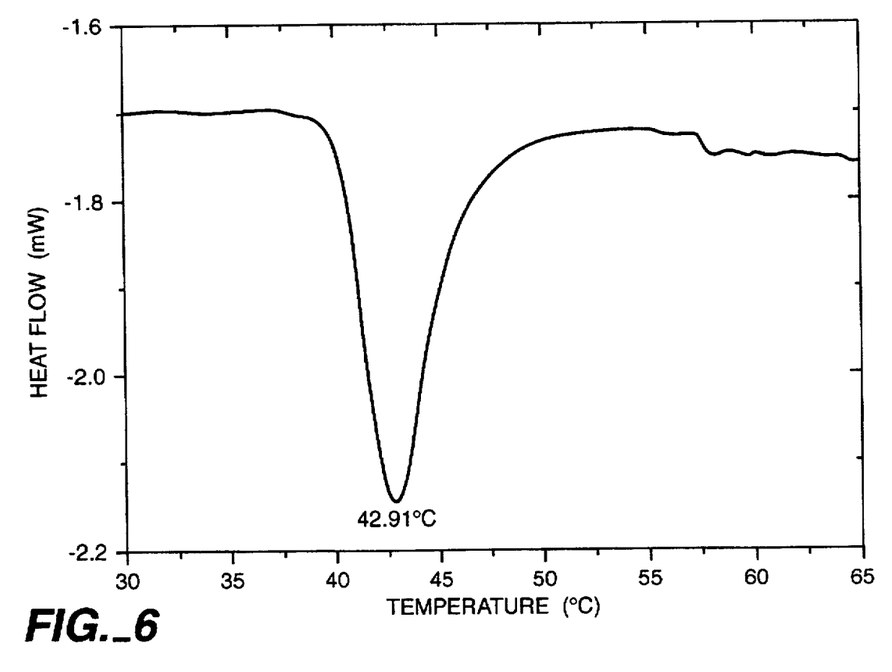
FIG. 6 illustrates a DSC scan from 30° C. to 65° C. of an aqueous composition comprising 2.2 weight percent collagen and 16.7 mg/mL methotrexate. After formulation, the composition was stored at 4° C. for 1 month. Upon removal from the refrigerator, the composition was optically translucent and remained so even as the temperature of the material reached room temperature. A DSC scan of this material illustrates that this composition exhibits a single collagen transition temperature at about 43°C.

Specifically, FIG. 5 illustrates that the aqueous collagen composition comprising methotrexate and stored at room temperature has two collagen transition temperatures, the first at about 42° C. and the second at about 52.4° C. Contrarily, FIG. 6 illustrates that the same aqueous collagen composition stored under refrigeration for the same period of time has a single collagen transition temperature of about 43° C.

In view of the results of this example, methotrexate is a compatible cytotoxic drug.

Figure 7A:
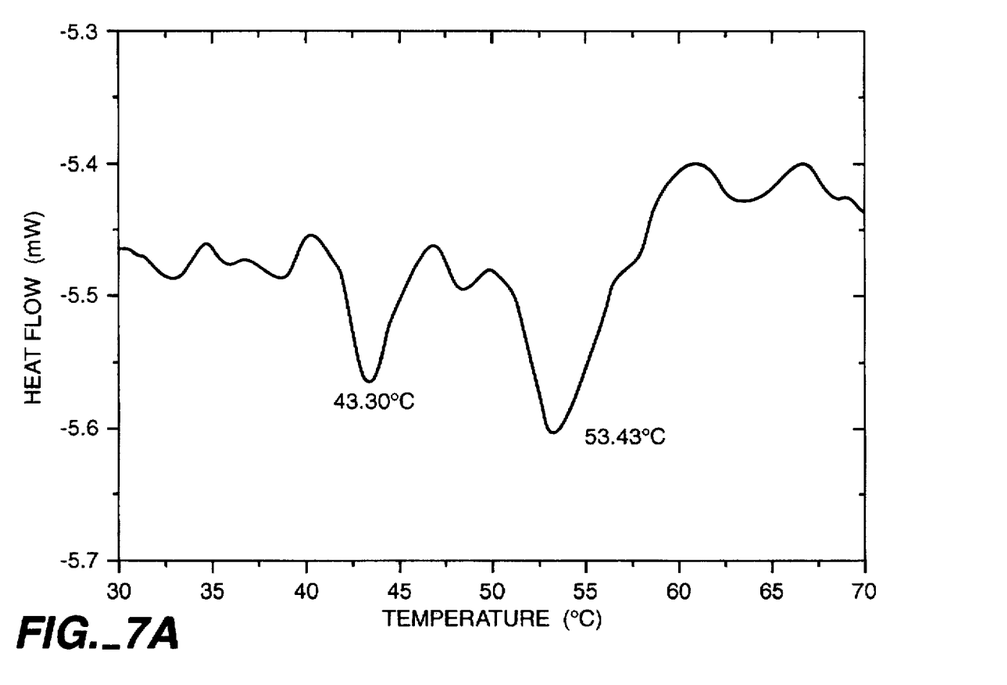
FIGS. 7A–7E illustrates DSC scans from 30° C. to 70° C. at 0 (FIG. 7A), 1 (FIG. 7B), 2 (FIG. 7C), 4 (FIG. 7D) and 8 (FIG. 7E) hours of an aqueous composition comprising 2 weight percent collagen and 0.4 weight percent cisplatin stored at room temperature. These scans illustrate the formation over time of a major collagen transition temperature at about 61° C. with a minor collagen transition temperature at about 43° C. for this composition.
Figure 7B:
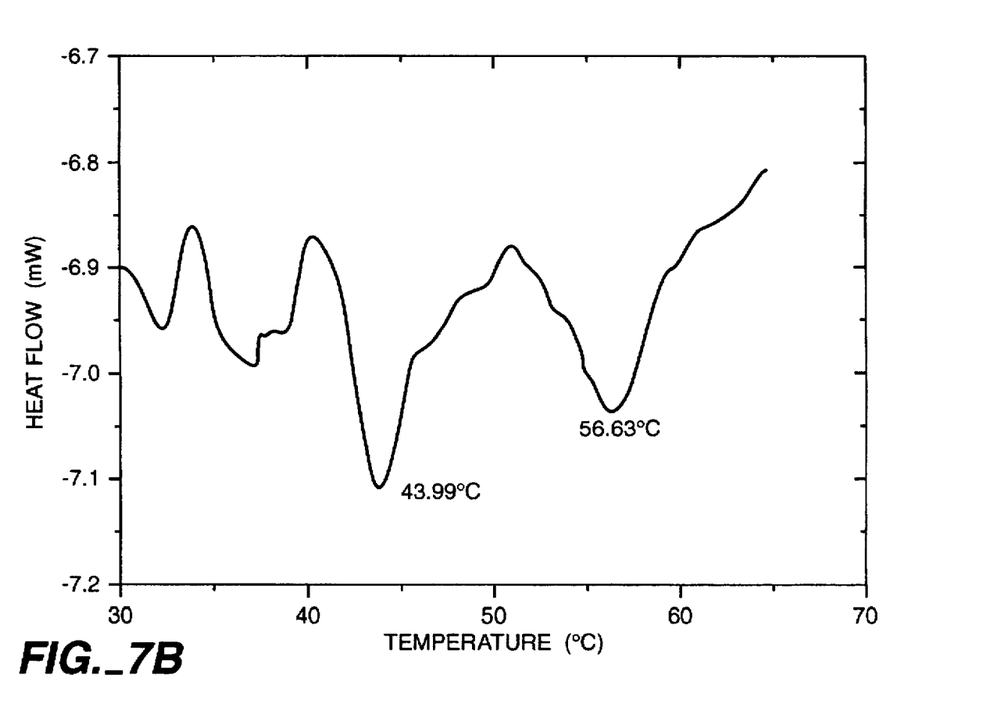
Figure 7C:
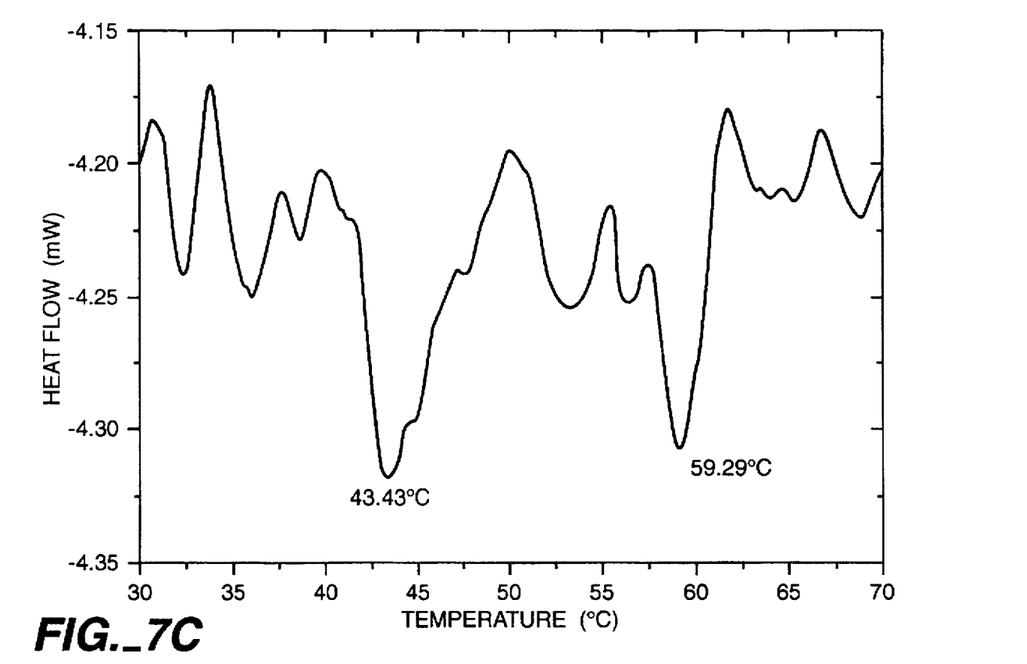
Figure 7D:
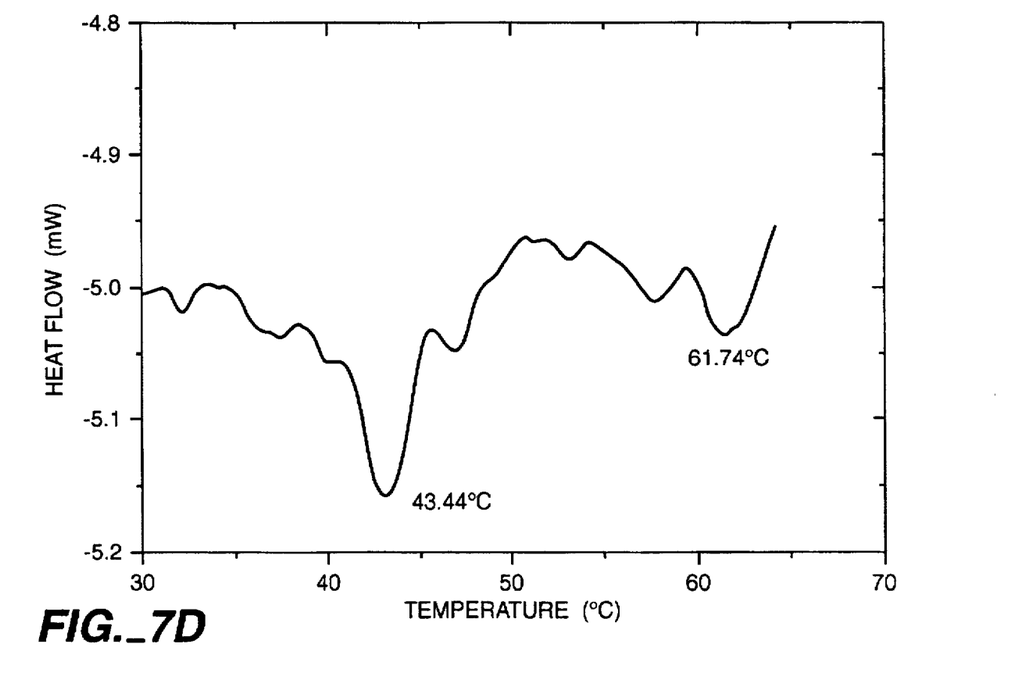
Figure 7E:
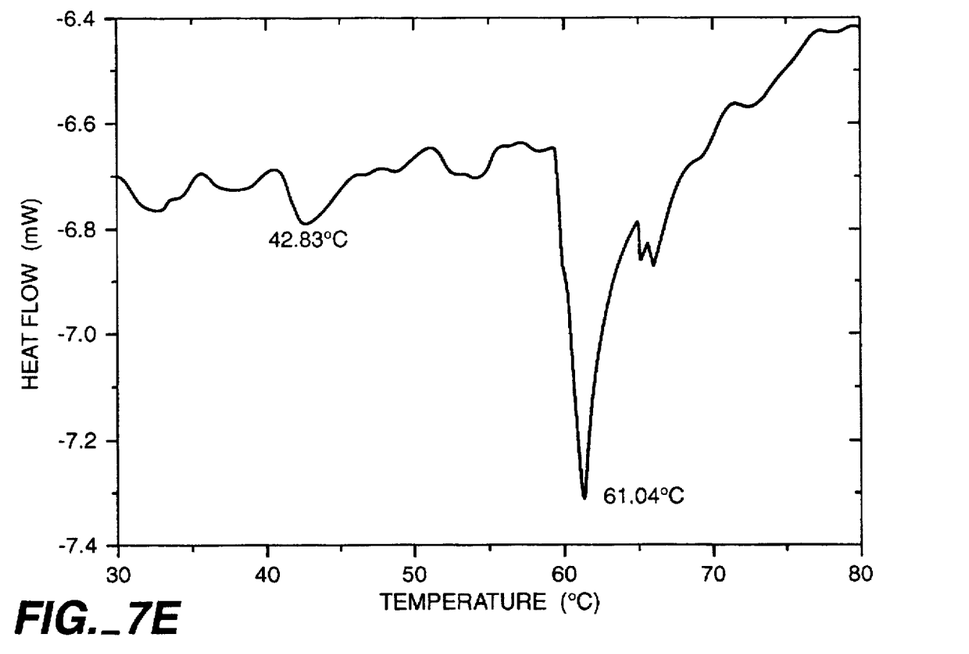

Example 3—Effect on the Collagen Transition Temperature of an Aqueous Collagen Composition Comprising Cisplatin An aqueous collagen composition was prepared as above with the exception that cisplatin was incorporated into the composition and the resulting composition contained collagen (2.2 weight percent), cisplatin (4 mg/mL), 0.033M sodium phosphates and 0.015M sodium chloride. The composition was stored at room temperature and DSC scans of aliquots of this composition were conducted as above at 0, 1, 2, 4 and 8 hours. The results of these scans are illustrated in FIGS. 7A (0 hour scan), 7B (1 hour scan), 7C (2 hour scan), 7D (4 hour scan) and 7E (8 hour scan).

Specifically, these figures illustrate that the initial transition temperatures of about 43° C. and 53° C. eventually give way over time to a major transition temperature peak of about 61 ° C. with only a minor peak remaining at 43° C. This increase in the transition temperature over time is construed to correlate to cross-linking (i.e., covalent bonding) of the cisplatin to the collagen in the aqueous collagen composition.

In view of the results of this example, cisplatin is not a compatible cytotoxic drug.

The results of Examples 1–3 illustrate that certain but not all cytotoxic drugs are compatible with collagen and permit the aqueous collagen composition to have a single transition temperature of 45° C. or less. Whether a cytotoxic drug is compatible in the collagen composition can be determined via standard DSC scans of the composition at various times when the composition is maintained at room temperature.

Alternatively, compatibility can be determined by generation of a single transition temperature of about 45° C. or less for collagen compositions comprising a candidate cytotoxic drug. It is understood that candidate cytotoxic drugs are those drugs for which a determination as to their compatibility in the methods and compositions of this invention is being made.

Example 4—Effect of Storage Temperature on Optical Opacity of Aqueous Collagen Composition Comprising Fluorouracil Three identical aqueous collagen compositions were prepared by combining requisite amounts of components under aseptic conditions to provide for an aqueous collagen composition comprising collagen (2.2 weight percent), fluorouracil (33.3 mg/mL), 0.033M sodium phosphates and 0.015M sodium chloride. Aliquots (0.5 mL) of each of the compositions were placed in microcuvet having a 1 mm pathlength at different temperatures for 10 minutes wherein the first aliquot was stored at about 12° C, the second aliquot was stored at about 8° C. and the third aliquot was stored at about 4° C. The optical opacity of each sample was then measured at 30 second intervals by determining the absorbance of light (410 nm) through the microcuvet. Lower absorbance in each case corresponds to greater optical clarity at 410 nm.

Figure 8:
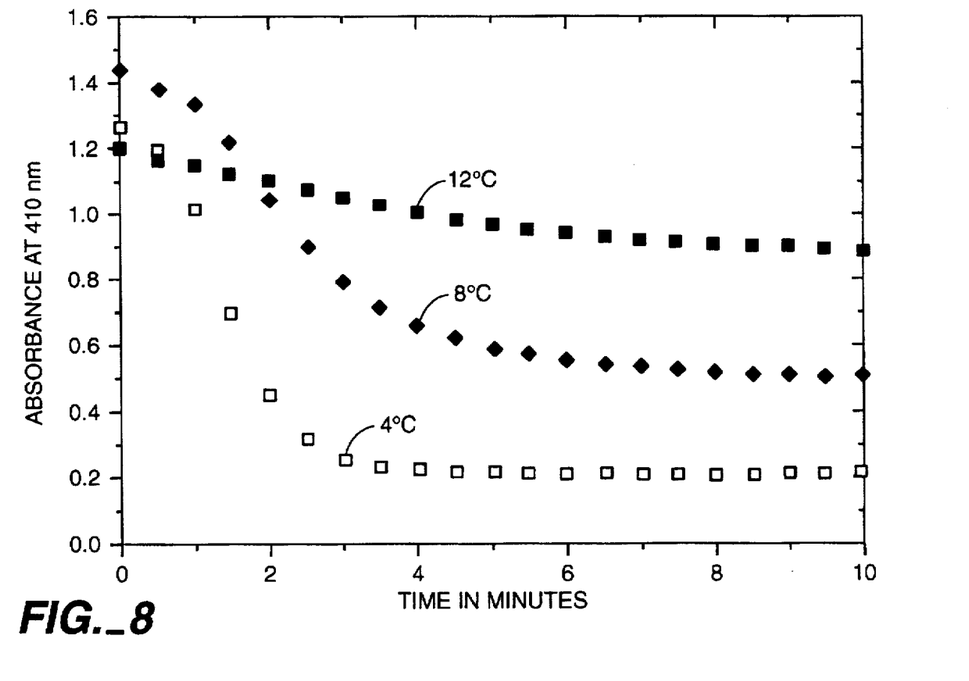
FIG. 8 illustrates the effects on optical opacity as measured by the absorbance of an aqueous collagen composition comprising 2.2 weight percent collagen and 33.3 mg/mL of fluorouracil due to storage at three different temperatures.

The results of this example are set forth in FIG. 8 which illustrates that storage of the aqueous collagen composition at either 4° or 8° C. results in significant reduction in absorbance of the sample over the storage time indicative of increased optical clarity of the sample. Contrarily, storage of the aqueous collagen composition at 12° C. did not result in a significant reduction in the absorbance of the sample. These results indicate that for aqueous collagen compositions comprising fluorouracil, storage at reduced temperatures requires, for this composition, storage at about 10° C. or less, and preferably at about 8° C. or less, to effect optical clarity.

Example 5—Effect of Cytotoxic Drug Concentration on Optical Opacity of Aqueous Collagen Composition Three identical aqueous collagen compositions were prepared as above with the exception that the amount of fluorouracil incorporated into the compositions were varied to be 16.65 mg/mL, 22.2 mg/mL and 33.3 mg/mL respectively. The resulting compositions were stored at 4° C. as aliquots (0.5 mL) in microcuvets having a 1 mm pathlength for 10 minutes and the optical opacity of each sample was measured at 30 second intervals by determining the absorbance of light (410 nm) through the microcuvet. Lower absorbance in each case corresponds to greater optical clarity at 410 nm.

Figure 9:
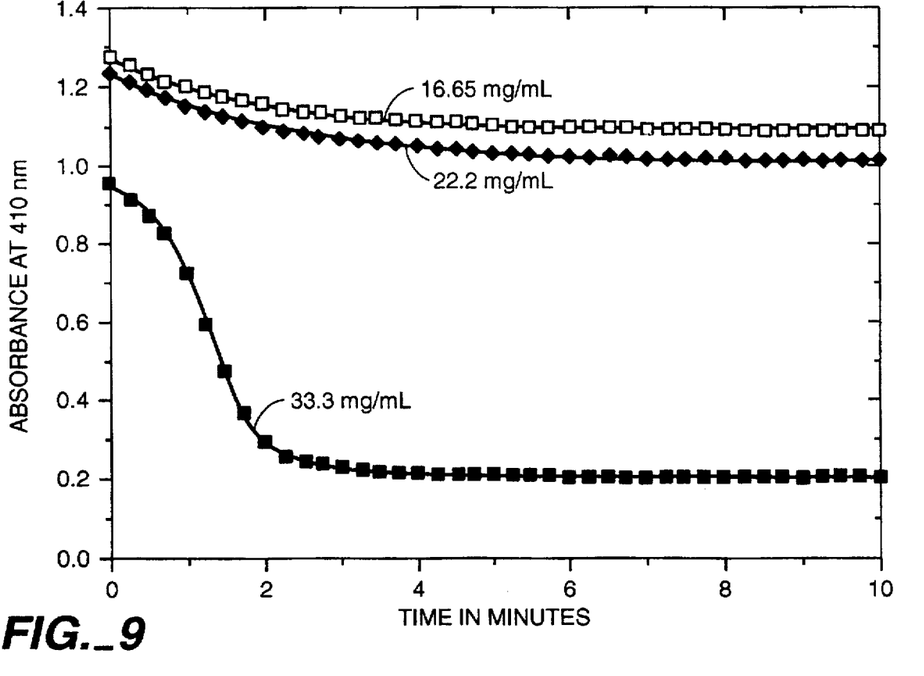
FIG. 9 illustrates the effects on optical opacity as measured by the absorbance of aqueous collagen compositions containing three different amounts of fluorouracil wherein each composition was then stored at 2–8° C.

The results of this example are set forth in FIG. 9 which illustrates that the collagen composition containing fluorouracil (33.3 mg/mL) has significantly lower absorbance as compared to the collagen compositions containing fluorouracil at either 22.2 mg/mL or 16.65 mg/mL. These results indicate that for aqueous collagen compositions comprising fluorouracil, an effective amount of fluorouracil is required to effect optical translucency.

A second study was conducted to determine the amount of fluorouracil required to effect clarification on an opaque aqueous collagen composition. Specifically, aqueous collagen compositions were formulated to contain collagen (21.7 mg/mL), 0.033M phosphate buffer and varying amounts of fluorouracil. Each composition was then stored at about 2° C. to 8° C. for 17 days and the optical appearance of the composition measured periodically. The results of this analysis are set forth in Table II below:

TABLE II

| FU conc. (mg/mL) | appearance (initial) | appearance (3 hrs.) | appearance (24 hrs.) | appearance (10 days) | appearance (17 days) |
|---|---|---|---|---|---|
| 33.3 | opaque | clear | clear | clear | clear |
| 20.0 | opaque | opaque | opaque | less opaque | less opaque |
| 6.7 | opaque | opaque | opaque | opaque | opaque |
| 0 | opaque | opaque | opaque | opaque | opaque |

The above data indicates that at 20 mg/mL, fluorouracil begins to has some clarifying affect on the opaque collagen composition. Accordingly, in a preferred embodiment, the concentration of fluorouracil is greater than about 20 mg/mL.

Example 6—Alternative Means to Obtain Optical Clarity in an Aqueous Collagen Composition The purpose of this example is to demonstrate that in some cases alternative means for obtaining optical clarity for aqueous collagen compositions can be used for certain compatible cytotoxic drugs. Specifically, in this example, the concentration of methotrexate in the collagen composition was varied and the collagen compositions were stored for 1 day and 3 days at either at 2° C. to 8° C. or at room temperature. The results at 3 days were the same as those found after 1 day and, accordingly, Table III below sets forth only the results from day 1.

TABLE III

| Methotrexate Concentration | Optical Properties when Stored at RT for 1 day | Optical Properties when Stored at 2° to 8° C. for 1 day |
|---|---|---|
| 1.0 mg/mL | white yellow, opaque | white yellow, opaque |
| 5.0 mg/mL | light yellow, opaque | light yellow, opaque |
| 10.0 mg/mL | light yellow, opaque | light yellow, slightly opaque |
| 16.7 mg/mL | yellow, opaque | yellow, semi-clear |
| 33.3 mg/mL | dark yellow, clear | dark yellow, clear |

The above results indicate that for methotrexate, both refrigeration and high concentrations of methotrexate are effective in effecting optical clarity. However, it appears that refrigeration provides enhanced optical clarity for methotrexate concentrations at 10 mg/mL and 16.7 mg/mL.

The purpose of Examples 7 and 8 which follow is to illustrate that the clarification phenomenon correlates to the presence of an effective amount of the compatible cytotoxic drug and not to other components in the composition. Specifically, since the fluorouracil formulation of Example 1 above has a pH of 9.3 (relative to a pH of 7.3 prior to addition of the fluorouracil), Example 7 was conducted to determine whether the pH has a significant clarification affect on an optically opaque collagen composition not containing a cytotoxic drug.

Since the addition of fluorouracil to the collagen composition of Example 2 above alters the concentration of the phosphate buffer and sodium chloride, Example 8 was conducted to determine whether the presence of different components other than fluorouracil has a significant clarification affect on an optically opaque collagen composition.

Example 7—Affect of Buffer and pH on Clarification of Optically Opaque Collagen Compositions A first study was conducted by preparing a first aqueous collagen composition which was formulated to contain 6.5 weight percent collagen, 0.1M sodium phosphate and 0.045M sodium chloride and had a pH after formulation of 7.3. A second aqueous collagen composition was formulated to contain 6.5 weight percent collagen, 0.1M sodium borate and 0.045M sodium chloride and had a pH after formulation of 9.1. Both compositions were then stored at from about 2° to 8° C. as aliquots (0.5 mL) in microcuvets having a 1 mm pathlength for 10 minutes and the optical opacity of each sample was measured at 15 second intervals by determining the absorbance of light (410 nm) through the microcuvet.

Lower absorbance in each case corresponds to greater optical clarity at 410 nm.

Figure 10:
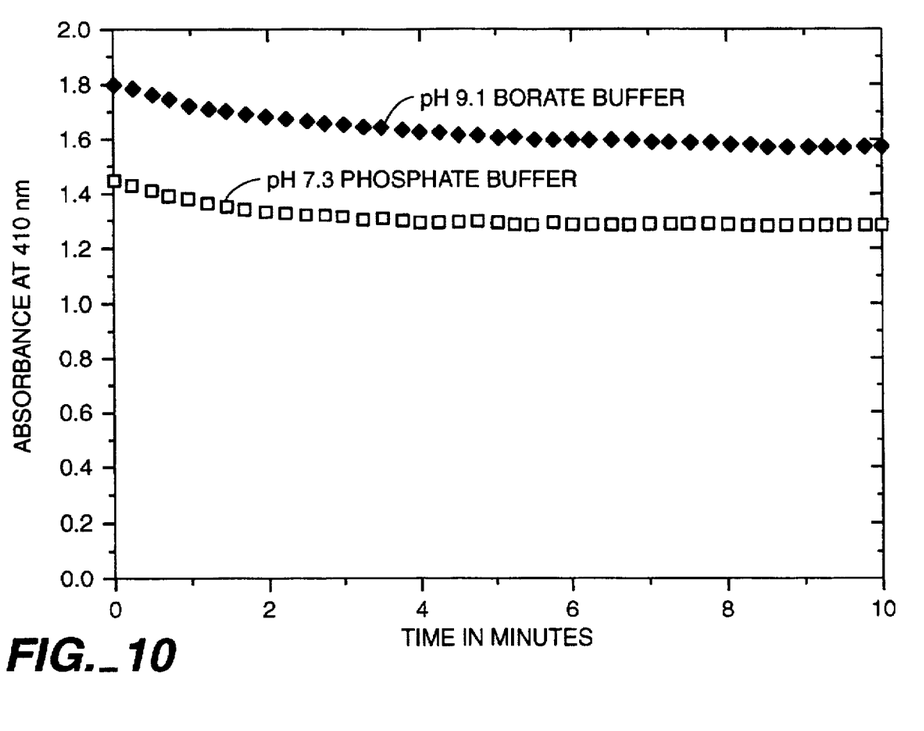
FIG. 10 illustrates the effects on optical opacity as measured by the absorbance of aqueous collagen compositions at two different pHs wherein each composition was then stored at 2–8° C.

The results of this analysis are set forth in FIG. 10 which illustrates that neither composition exhibited a material change in absorbency during storage which is indicative that neither the pH nor the buffer has a significant clarification affect on an optically opaque collagen composition not containing a cytotoxic drug.

A second study was conducted by preparing collagen compositions having 0.033M potassium phosphate buffer and 21.7 g collagen. The pH of the solution was adjusted by the addition of HCl or NaOH as necessary to modify the pHs of the compositions to approximately 5, 7, 8 and 9. The compositions were stored at either room temperature or at 2-8° C. The optical appearance of these compositions was evaluated at 1 and 11 days after storage. The results of this evaluation are set forth in Table IV below:

TABLE IV

| pH of Comp. | appearance at day 1 for storage at RT | appearance at day 1 for storage at 2°–8° C. | appearance at day 11 for storage at RT | appearance at day 11 for storage at 2°–8° C. |
| --- | --- | --- | --- | --- |
| 4.87 | milky white | milky white | milky white | milky white |
| 6.98 | opaque white | opaque white | opaque white | opaque white |
| 8.07 | opaque white | opaque white | opaque white | opaque white |
| 8.90 | opaque white | opaque white | opaque white | opaque white |

The results of Table IV above indicate that the pH does not have a significant affect on clarification of optical opaque collagen compositions although, at pH 5, the collagen composition is less opaque as compared to collagen compositions having a neutral or basic pH. However, no clarification of any sample was observed during storage at either room temperature or at 2° to 8° C.

Example 8—Affect of Additives on Clarification of Optically Opaque Collagen Compositions The affect of additives on clarification of opaque aqueous collagen compositions was determined using different additives. Specifically, the additives urea, sucrose, sodium chloride, glycerol and fluorouracil were incorporated into separate compositions comprising 6.5 weight percent collagen, 0.25M of the additive and sufficient sodium borate to provide a pH of 9.1.

Figure 11:
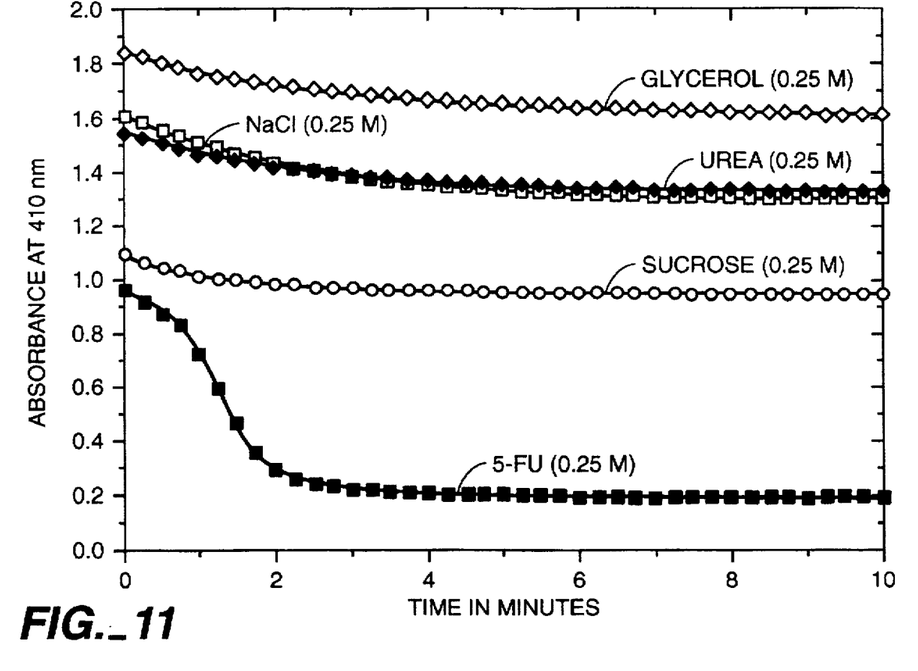
FIG. 11 illustrates the effects on optical opacity as measured by the absorbance of aqueous collagen compositions employing different components added at 0.25M and then stored at 2–8° C.

Each composition was then stored at from about 2° to 8° C. as aliquots (0.5 mL) in microcuvets having a 1 mm pathlength for 10 minutes and the optical opacity of each sample was measured at 15 second intervals by determining the absorbance of light (410 nm) through the microcuvet. Lower absorbance in each case corresponds to greater optical clarity at 410 nm. The results of this analysis are set forth in FIG. 11 which illustrates that only fluorouracil has any significant effect on clarifying the collagen composition during storage at from about 2° to 8° C.

Example 9—Enhanced Retention of Compatible Cytotoxic Drug at Site of Injection

The retention at the site of injection of an optically translucent fluorouracil/collagen composition prepared per this invention was compared against that of an optically opaque fluorouracil composition.

Preparation of Optically Translucent Fluorouracil/Collagen Composition

Aqueous collagen gel compositions containing collagen (22.4 mg/mL), fluorouracil (33.3 mg/mL), 0.033M sodium phosphates, and 0.015M sodium chloride, with the pH adjusted to about 9.3 were stored in syringes (nominal fill 0.9 mL) at a temperature of from about 2° C. to 8° C for not less than 24 hours to provide for an optically translucent composition.

An aqueous solution containing epinephrine (1 mg/mL), edetate disodium (0.5 mg/mL), sodium metabisulfite (1.5 mg/mL) and sodium chloride (8 mg/mL) was stored in a second syringe (nominal fill 0.1 mL).

A final gel for injection into a lesion was prepared by connecting a fluorouracil gel syringe with an epinephrine solution syringe and transferring the contents thereof back and forth by syringe-to-syringe transfer through a mixing adapter connecting the two syringes until the composition was homogenous. The resulting optically translucent gel preparation contains fluorouracil (30 mg/mL), epinephrine (0.1 mg/mL), collagen (20 mg/mL), 0.03M sodium phosphates, sodium chloride (1.6 mg/mL), edetate disodium (0.05 mg/mL), sodium metabisulfite (0.15 mg/mL) and has a pH of about 9. This gel was used within 1 hour of preparation.

Preparation of Optically Opaque Fluorouracil/Collagen Composition

Aqueous collagen gel compositions containing collagen (65 mg/g), 0.1M sodium phosphates, and 0.045M sodium chloride, with the pH adjusted to about 7.2 were stored in a first container (0.3 mL in a prefilled syringe) and these compositions were optically opaque both before and after storage.

An aqueous solution containing epinephrine (1 mg/mL), edetate disodium (0.5 mg/mL), sodium metabisulfite (1.5 mg/mL) and sodium chloride (8 mg/mL) was stored in a second container.

An aqueous solution containing fluorouracil (50 mg/mL) was stored in a third container.

A final gel for injection into a lesion was prepared by mixing the contents of the three containers until the composition was homogenous. The resulting optically opaque gel preparation contains fluorouracil (30 mg/mL), epinephrine (0.1 mg/mL), collagen (20 mg/mL), 0.03M sodium phosphates, sodium chloride (1.6 mg/mL), edetate disodium (0.05 mg/mL), sodium metabisulfite (0.15 mg/mL) and has a pH of about 9. This optically opaque gel composition was used within 1 hour of preparation.

Retention Study

The optically opaque and optically translucent collagen compositions prepared as above were then evaluated for local retention using a syngeneic fibrosarcoma (RIF-1), implanted and grown dermally in mice. In this evaluation, tumor cells were injected subdermally in the flanks, the resultant tumors were grown to a visible size (typically about 0.5 cm$^3$), then the animals were treated via intratumoral injection of one or the other collagen compositions described above with $^3$H-labeled fluorouracil. Tumors were excised after various time periods between zero and 24 hours, the tissue digested, and the amount of $^3$H in the tissue determined by scintillation counting. An area under the tumor content/time curve (AUC) is calculated and used as a measure of cumulative exposure of the tissue to the drug.

Figure 12:
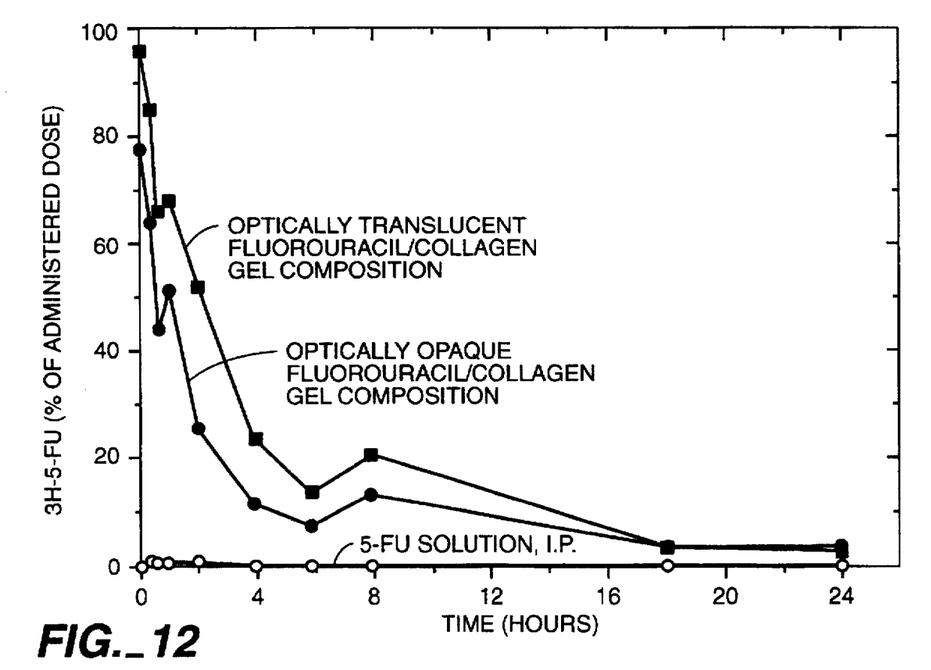
FIG. 12 illustrates the improved retention of fluorouracil at the site of injection achieved by use of the compositions described herein.

The results of this study are set forth in FIG. 12 which graphically illustrates retention of labeled fluorouracil at the site of injection over time. Specifically, the Y axis reflects retention in the tumor (as a percent of administered dose) of labeled fluorouracil whereas the X axis reflects time from initial administration. The results of this figure illustrate that the optically clear composition provides for 30% to 50% higher tumor AUC than does the optically opaque composition. The relative standard error of the AUC. in this study was determined to be in the range of 25 to 35%. Accordingly, these results indicate that the optically clear collagen gel composition containing the same concentration of fluorouracil as the optically opaque composition provides for better retention of this cytotoxic drug at the site of injection as compared to the optically opaque composition.

FIG. 12 also illustrates tumor AUC. arising from administering an aqueous solution of fluorouracil intraperitoneally to the mice. As is readily apparent, this route of administration is significantly less suitable than either use of the optically opaque or optically translucent compositions.

It is contemplated that these results will also translate to enhanced efficacy of the fluorouracil in the optically clear collagen composition as compared to the optically translucent collagen gel compositions with corresponding less side effects due to migration of the fluorouracil from the site of injection.

What is claimed is:

1. An optically translucent proteinaceous composition in which the protein component comprises from about 30% to about 100% of collagen, which protein component is dispersed in an aqueous medium to provide an amorphous flowable mass having a collagen concentration of from about 5 to about 100 mg/ML and an effective amount of a compatible cytotoxic drug to render the composition optically translucent wherein the collagen in said proteinaceous composition has a single transition temperature in the temperature range of from 30° C. to about 45° C.

2. The proteinaceous composition according to claim 1 wherein said compatible cytotoxic drug is selected from the group consisting of fluorouracil and methotrexate.

3. The proteinaceous composition according to claim 2 wherein the cytotoxic drug is fluorouracil.

4. The proteinaceous composition according to claim 3 wherein the concentration of fluorouracil is greater than about 20 mg per mL of aqueous composition.

5. The proteinaceous composition according to claim 2 wherein the cytotoxic drug is methotrexate.

6. The proteinaceous composition according to claim 5 wherein the concentration of methotrexate is at least about 10 mg per mL of aqueous composition.

7. The proteinaceous composition according to claim 1 which composition further comprises a vasoconstrictor drug.

8. The proteinaceous composition according to claim 7 wherein said vasoconstrictor drug is selected from the group consisting of epinephrine, norepinephrine, epinephryl borate and dipivefrin.

9. A method for treating a neoplastic lesion or surrounding tissue which method comprises:

introducing at the site of the lesion or tissue surrounding the lesion an optically translucent proteinaceous composition capable of stable placement, which composition comprises collagen dispersed in an aqueous medium at a concentration of from about 5 to about 75 mg/mL to provide an amorphous flowable mass and including a sufficient concentration of a compatible cytotoxic drug uniformly dispersed therein so that said collagen has a single transition point in the temperature range of from 30° C. to about 45° C. and said composition is optically translucent whereby said drug is slowly released into the immediate environment thereby avoiding significant levels of the drug at sites distant from the site of introduction.

10. The method according to claim 9 wherein said compatible cytotoxic drug is selected from the group consisting of fluorouracil and methotrexate.

11. The method according to claim 10 wherein the cytotoxic drug is fluorouracil.

12. The method according to claim 11 wherein the concentration of fluorouracil is greater than about 20 mg per mL of aqueous composition.

13. The method according to claim 10 wherein the cytotoxic drug is methotrexate.

14. The method according to claim 13 wherein the concentration of methotrexate is at least about 10 mg per mL of aqueous composition.

15. The method according to claim 9 wherein the composition further comprises a sufficient amount of a vasoconstrictor drug to constrict capillaries in the vicinity of the lesion or tissue surrounding the lesion.

16. The method according to claim 15 wherein said vasoconstrictor drug is selected from the group consisting of epinephrine, norepinephrine, epinephryl borate and dipivefrin.

17. A method for preparing an aqueous collagen composition optically translucent at room temperature wherein the collagen has a single transition point in the temperature range of from 30° C. to about 45° C. which method comprises:

(a) adding a proteinaceous material in which the protein components comprise from about 30% to about 100% of collagen dispersed in an aqueous medium at a concentration of from about 5 to about 75 mg/mL to provide an amorphous flowable mass;

(b) combining an effective amount of a compatible cytotoxic drug so that said collagen composition becomes optically translucent when said composition is cooled to about 10° C. or less and said collagen in said composition has a single transition point in the temperature range of from 30° C. to about 45° C. ;

(c) cooling the composition produced in (b) above to a temperature of about 10° C. or less for a sufficient period of time such that the composition becomes optically translucent; and (d) allowing the composition to come to room temperature.

18. The method according to claim 17 wherein said compatible cytotoxic drug is selected from the group consisting of fluorouracil and methotrexate.

* * * * *